United States Patent [19]

Cohen

[11] Patent Number: 4,735,212
[45] Date of Patent: * Apr. 5, 1988

[54] MULTIPLE SITE FIBER OPTIC PRESSURE TRANSDUCER

[75] Inventor: Donald M. Cohen, Miami, Fla.

[73] Assignee: Cordis Corporation, Fla.

[*] Notice: The portion of the term of this patent subsequent to Sep. 8, 2004 has been disclaimed.

[21] Appl. No.: 889,421

[22] Filed: Jul. 23, 1986

Related U.S. Application Data

[63] Continuation-in-part of Ser. No. 881,476, Jul. 1, 1986, Pat. No. 4,703,757, which is a continuation of Ser. No. 671,913, Nov. 16, 1984, abandoned.

[51] Int. Cl.$^4$ .............................................. A61B 5/02
[52] U.S. Cl. .................................. 128/667; 128/675; 128/748; 73/705; 250/231 P
[58] Field of Search ............... 128/748, 667, 673, 675, 128/634; 73/705; 350/96.32, 96.33; 250/231 P

[56] References Cited

U.S. PATENT DOCUMENTS

| | | | |
|---|---|---|---|
| 3,051,003 | 8/1962 | Witt | 73/705 |
| 4,201,222 | 5/1980 | Haase | 128/634 |
| 4,487,206 | 12/1984 | Aagard | 128/634 |
| 4,543,961 | 10/1985 | Braun | 128/748 X |

Primary Examiner—William E. Kamm
Assistant Examiner—John C. Hanley
Attorney, Agent, or Firm—Tarolli, Sundheim & Covell

[57] ABSTRACT

Apparatus is provided for simultaneously measuring fluid pressure at multiple sites at remote locations within a body cavity. A single elongated optical fiber capable of being inserted into such a body cavity is employed and which has a light transmitting core which is coaxially surrounded by cladding means essentially throughout its length. The core is uncladded at a plurality of portions of its length near the distal end thereof. A pressure transducer is located at each of the uncladded core portions. Each pressure transducer includes a flexible transducer member having an irregular surface facing the uncladded core portion for making surface area contact therewith so that the contacting surface area varies with applied pressure. The transducer member is constructed of material exhibiting a greater index of refraction than the cladding means and selective optical absorption so that the intensity of light passing through the core proximate to the transducer member is modulated in intensity as a function of the pressure. Each transducer includes light wavelength dependent means for modulating light at a particular wavelength different from that of the other transducers.

14 Claims, 5 Drawing Sheets

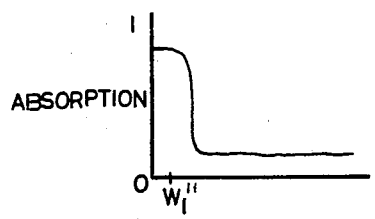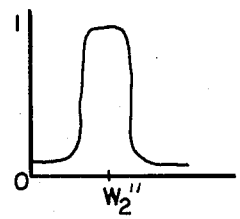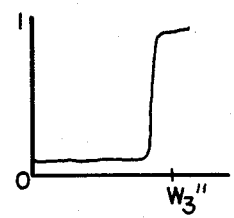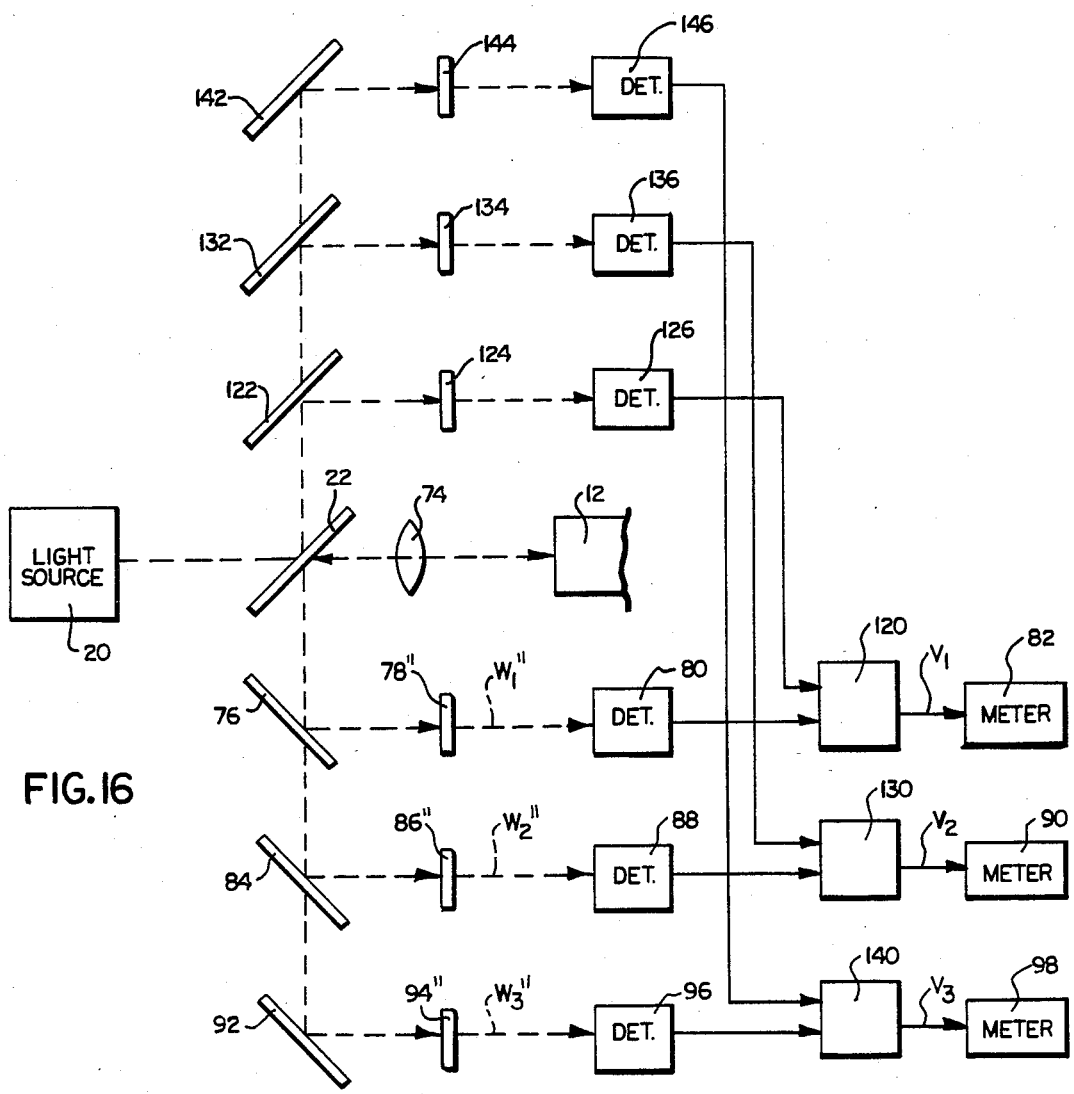

MULTIPLE SITE FIBER OPTIC PRESSURE TRANSDUCER

RELATED APPLICATION

This is a continuation-in-part of my previously filed U.S. application Ser. No. 881,476 filed July 1, 1986 now U.S. Pat. No. 4,703,757, and which in turn was a continuation of application Ser. No. 671,913 filed Nov. 16, 1984, now abandoned.

BACKGROUND OF THE INVENTION

This invention relates to the art of measuring body fluid pressure, such as blood pressure, within the cardiovascular system, and, more particularly, to apparatus for directly measuring the body fluid pressure at multiple sites of interest by means of a catheter having a single optical fiber therein with multiple pressure transducers for simultaneously sensing pressure at different sites.

It is known in the art to employ catheter tip transducers insertable into a blood stream for purposes of providing direct pressure monitoring at the location of interest. Many of such catheter tip transducers employ semiconductors and other sensing elements requiring an electrical signal to be carried by wires throughout the length of the catheter from the site of interest to a location externally of the body being tested. Such semiconductor tip transducers require the use of electricity to power the sensor. The use of electricity not only renders the device susceptible to electromagnetic interference, but also introduces the possible hazard of arrhythmia induction.

To overcome some of the noted difficulties, other devices for determining blood pressure in the cardiovascular system have included catheters employing optically based pressure transducers at the distal end. Such devices typically take the form as illustrated and described in U.S. Pat. Nos. 3,249,105 and 3,215,135, to Polyanyi and Franke. Each of these devices employs a catheter having fiber optic means extending the length of the catheter to the distal end thereof at which the fiber optic means is in optical communication with a pressure transducer. However, each of these devices is limited to measuring the pressure at a single site at a time. If pressure readings are required at different sites, then the readings must be taken at different times and the catheter must be moved so that its tip transducer at the distal end is moved from site to site.

It is often desirable to measure intravascular pressure at more than one site, the readings being taken simultaneously. One device known in the prior art capable of performing this function has been disclosed in U.S. Pat. No. 4,543,961 to D. C. Brown, assigned to the same assignee as the present invention. In Brown, supra, there is provided an elongated catheter having a plurality of optical fibers aligned end-to-end in the lumen of the catheter. A plurality of pressure transducers are provided along the length of the catheter with each being associated with the spacing between two aligned optical fibers. The pressure transducer includes a filter-mirror which is movable between the adjacent ends of two spaced apart fibers, the movement being in response to pressure acting against the catheter. Light is directed into the proximal end of the catheter and is transmitted by the optical fibers. At each pressure transducer, light of one wavelength will be reflected by a filter-mirror back to the proximal end in accordance with the pressure exerted on the transducer at that site. Each filter-mirror reflects only one selected color and transmits other colors. Consequently, at the proximal end, the reflected light of three different colors may be individually examined to determine the pressure exerted at each of the three sites under examination.

The present invention is directed to improvements over that disclosed in Brown, supra. The construction in Brown employs a plurality of optical fibers aligned end-to-end within the lumen of an elongated flexible catheter. This results in difficulty of construction, since a typical catheter may have a diameter on the order of 0.06 inches and the optical fiber carried therein may be on the order of 400 micra. Placing a plurality of such fibers in end-to-end alignment along with associated filter-mirrors within such a catheter presents substantial difficulty in manufacture.

The present invention is similar to that discussed in Brown, supra, but permits the use of a single elongated fiber, together with a plurality of pressure transducers associated with the fiber in such a manner that the fiber is not interrupted at the location of each transducer, as in the case of Brown. This is achieved in the present invention by employing pressure transducers based on that described in my previously filed U.S. application Ser. No. 671,913, supra. The transducer disclosed therein is constructed of flexible, optically absorbent material having a portion thereof which makes variable surface area contact with an uncladded core portion of the optical fiber in dependence upon transversely applied pressure forces. The variations in surface contact area cause changes in the light refraction characteristics and this modulates the intensity of light passing through the core proximate thereto. The use of a plurality of such transducers located at spaced apart locations on an elongated single optical fiber achieves a multiple site fiber optic pressure transducer system which is easier to manufacture and has a faster frequency response than that of the prior art discussed hereinabove.

SUMMARY OF THE INVENTION

It is an object of the present invention to provide an improved multiple site fiber optic pressure transducer system employing a single elongated optical fiber together with a plurality of pressure transducers for measuring fluid pressure at different remote sites within a body cavity.

It is a still further object of the present invention to provide an improved optical fiber pressure transducer system adapted for side port blood pressure monitoring at a plurality of locations and which is constructed in a manner so that it is sufficiently inexpensive to be disposable.

It is a still further object of the present invention to provide an improved multiple site fiber optic pressure transducer system employing a plurality of pressure transducers operating on a single elongated optical fiber so that pressure acting transversely of the optical fiber at different sites may be measured simultaneously.

The present invention contemplates the use of a single elongated flexible fiber optic member having a light transmitting core coaxially surrounded by cladding means essentially throughout its length. The core is uncladded for a plurality of spaced apart portions of its length. A pressure transducer means is located adjacent each of the uncladded portions with the pressure transducer means being constructed of flexible material having an index of refraction greater than that of the cladding means. Each transducer means has a surface portion which faces the adjacent uncladded core portion and makes surface area contact therewith such that the contacting surface area varies with pressure forces applied to the transducer means acting transversely of the uncladded core portion. In this manner, the intensity of any light passing through the core portion proximate to the contact surface area may be modulated as a function of the magnitude of the pressure.

In accordance with one aspect of the present invention, each pressure transducer means is doped with a different fluorescent dye such that each transducer means fluoresces in a different waveband. At each pressure transducer site, as the pressure increases more light is refracted into the flexible material including that of the wavelength which excites the fluorescent dye causing an increase in the emitted light at the emission wavelength at that site. The information from the various sites is detected externally of the proximal end of the optical fiber to obtain the pressure readings at the various sites.

In accordance with another aspect of the present invention, a filter coating is applied to each of the uncladded core portions between the pressure transducer means and the core of the optical fiber. Each filter transmits light in one waveband and reflects all other wavebands with the various filters transmitting different wavebands. At each pressure transducer site, light passed by the filter is partially refracted into a flexible, variable contact area material as described previously, with the amount of light absorption of that waveband being dependent upon the magnitude of pressure applied. Detector circuitry may be located adjacent the proximal end of the optical fiber for determining the pressure levels at each of the various sites being monitored in dependence upon the amount of light that has been absorbed in each of the wavebands.

In accordance with a still further aspect of the present invention, a flexible filter coating is applied on the exterior side of each flexible, transparent, variable contact area transducer with each filter transmitting light within one waveband while reflecting the remaining light. Consequently, at each transducer site only light within a particular waveband is transmitted through the filter and not returned to the core with the rest of the light being reflected back into the core. The refractive index of the flexible transducer is to be intermediate to the core and cladding indices.

BRIEF DESCRIPTION OF THE DRAWINGS

The foregoing and other objects and advantages of the present invention will become more apparent from a consideration of the following description as taken in conjunction with the accompanying drawings, wherein:

FIGS. 15A-15C are waveforms showing light absorption with respect to wavelength which is useful in describing the embodiment of FIGS. 13 and 14; and FIG. 16 is a schematic-block diagram illustration of the detector circuitry employed in conjunction with the embodiment of FIGS. 13 and 14.

DETAILED DESCRIPTION OF PREFERRED EMBODIMENTS

Figure 1:
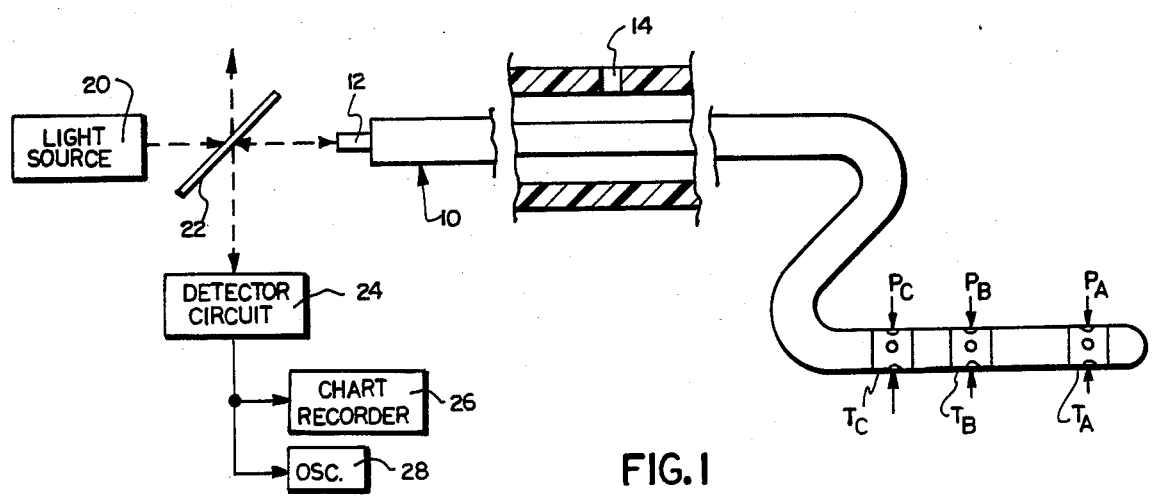
FIG. 1 is a schematic illustration of a multi-site pressure measuring catheter in conjunction with one application of this invention.

Reference is now made to the drawings wherein the showings are for purposes of illustrating preferred embodiments only, and not for limiting same. FIG. 1 illustrates an application of the invention as applied to measurement of blood pressure within a patient's cardiovascular system and includes an elongated single lumen catheter 10 containing an optical fiber 12 which extends throughout the length of the catheter. The catheter carries three blood pressure transducers $T_A$, $T_B$, and $T_C$ for simultaneously measuring the blood pressure within the cardiovascular system at three different sites, such as sites A, B and C. The spacing between the pressure transducers may be varied as desired and, for example, the transducer $T_A$ may be located adjacent the distal end of the catheter with transducers $T_B$ and $T_C$ spaced therefrom toward the proximal end. It is contemplated, for example, that these transducers may be used for simultaneous recording of pulmonary wedge pressure, right ventricular pressure, and atrial pressure. In such case, the transducers will be spaced approximately 10 centimeters apart.

As will be described in greater detail hereinafter with respect to each embodiment of the invention, each of the transducers serves to measure pressure acting in a direction transversely of the optical axis of the optical fiber. For this purpose, each transducer is provided with an array of side ports spaced equidistant apart circumferentially about the catheter with each side port being covered with an elastic membrane which may, for example, take the form of silastic. Each membrane covers a transducer member constructed of flexible material having an index of refraction which may be greater than that of the core of the optical fiber and is greater than the cladding thereon and serves to make surface area contact with an uncladded core portion of the optical fiber. The contacting surface area will vary with pressure applied to the transducer acting transversely of the optical axis of the optical fiber. As the pressure increases, more light will be refracted and absorbed by the transducer member. Consequently, any light entering the proximal end of the optical fiber 12 will be modulated in each of the pressure transducers in dependence upon the magnitude of the pressures applied at the transducer sites. A mirror surface is provided at the distal tip of tne optical fiber so that the light reflected therefrom is again modulated at the transducers as the light returns to the proximal end of the optical fiber. To assist in measuring pressure relative to atmospheric pressure, the catheter is vented, as with an aperture 14 in the wall of the catheter at a location near the proximal end where it is exterior to the patient.

In general, it is contemplated that for each embodiment herein, there will be provided a suitable light source 20 which transmits light into the proximal end of the optical fiber 12 so that the light may be modulated in dependence upon the pressure applied to each of the transducers $T_A$, $T_B$ and $T_C$. The input light may first pass through a beam splitter 22 which passes a portion of the light into the proximal end of the optical fiber 12 and directs the remaining light in an upward direction. Light that has been modulated and reflected from the distal end of the catheter is returned to the proximal end of the optical fiber 12 and is passed to the beam splitter 22 and a portion of this modulated light is then directed downwardly to an optical detector circuit 24. As will be described with respect to each embodiment, the detector circuitry operates to determine from the modulated light the values of the pressure $P_A$, $P_B$ and $P_C$ acting at the monitored sites A, B and C. This information may then be displayed as with the use of a conventional chart recorder 26 and/or displayed as with an oscilloscope 28. Having now provided a general description of one application of the invention, attention is directed to the specific description of each of the embodiments herein as presented below.

Figure 2:
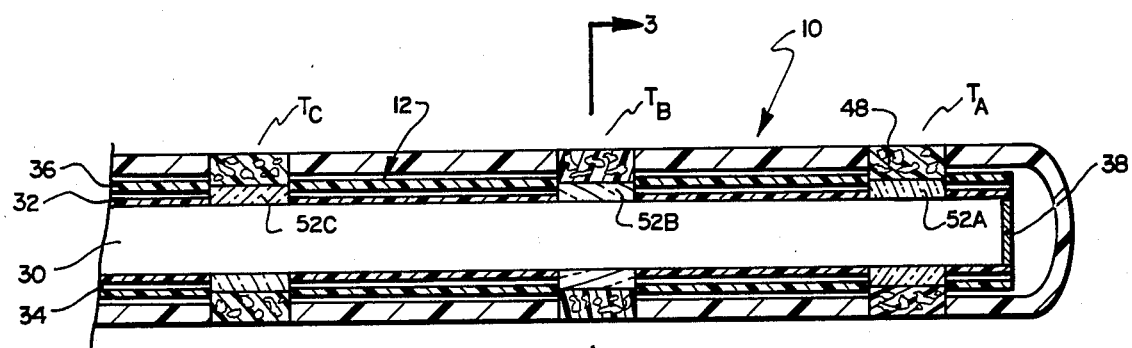
FIG. 2 is an enlarged sectional view of the distal end of the catheter in accordance with one embodiment of the invention.

Reference is now made to FIG. 2 which presents an enlarged sectional view of the distal end of catheter 10 and showing pressure transducers $T_A$, $T_B$ and $T_C$. As seen, the catheter 10 is a single lumen, thin wall catheter, such as that provided by Cordis Corporation, and known as Cordis FR5 Thin Wall Catheter. This catheter may have a diameter on the order of 0.066 inches and is constructed of plastic material, such as polyurethane. The optical fiber 12 carried within the single lumen of the catheter preferably takes the form of a cladded multimode optical fiber. This fiber has a core 30 of acrylic material of a diameter on the order of 368 micra. The core 30 is covered throughout essentially all of its length with cladding 32 constructed of a fluoropolymer having a thickness on the order of 16 micra. Surrounding the cladding 32 are Kevlar reinforcing strands 34 for purposes of strengthening the optical fiber 30. The Kevlar strands 34 are, in turn, covered with a layer of black Hytrel 36. Optical fibers, such as fiber 30, are commercially available. Light passing through the optical fiber 30 is reflected at the distal end by a mirror 38. This mirror is provided by depositing reflective material, such as silver, but not confined to metal, on the distal end of the core. This may be deposited as by sputtering, plating, the use of colloidal material or the use of a transparent adhesive attaching a reflective surface.

Figure 3:
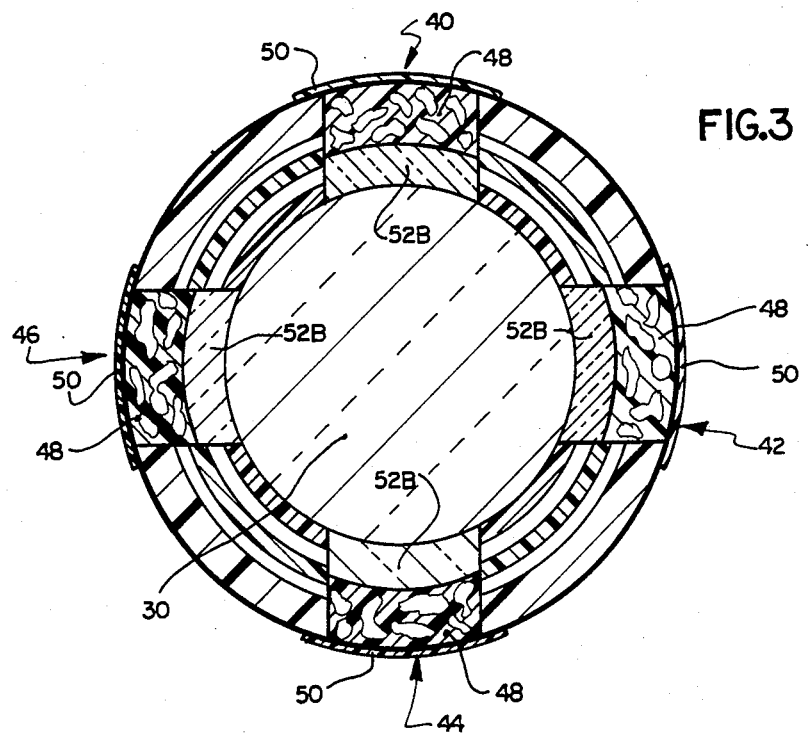
FIG. 3 is an enlarged sectional view taken along line 3—3 looking in the direction of the arrows of FIG. 2.

At the locations for each of the pressure transducers $T_A$, $T_B$ and $T_C$, the cladding is removed. At each location there are provided four side ports 40, 42, 44, and 46 spaced in an annular array equidistant from each other, as is best shown in FIG. 3, which is a cross sectional view taken along line 3—3 looking in the direction of the arrows in FIG. 2. On each of the side ports, the cladding 32 and strands 34 and coating 36 are removed and replaced with a sponge-like transducer insert 48. The outer surface of each insert may, in turn, be coated with a protective membrane 50 which may be of a latex material and may be formed by applying viscous liquid of latex over the insert filled side port in adjacent exterior surface areas of the catheter and then air drying it. The membrane, while covering the insert, will adhere and form a seal with the outer surface of the catheter, but will not adhere to the sponge-like material forming the transducer inserts.

In the embodiment shown in FIGS. 2 and 3, the inner surface of each transducer insert faces a portion of the uncladded surface of the optical core 30. Intermediate the insert and the uncladded core 30, there is provided an optical coating defining a filter. These filters are illustrated and identified as filters 52A, 52B and 52C.

The filters 52A, 52B and 52C are standard coatings with each filter having a different functional relationship between index of refraction and wavelength. Thus, these filters are so chosen that each will partially refract a different waveband and reflect all other wavebands. This will be discussed in greater detail hereinafter.

In the construction of the embodiment as shown in FIG. 2, the cladding is removed at the locations for transducers $T_A$, $T_B$ and $T_C$. This may be accomplished in a controlled manner, as with the use of a solvent, such as tetrahydrofuran, so that the removal takes place only at desired locations. The transducer inserts 48 are constructed of a sponge-like material, such as polyurethane foam. This may take the form of hypol foamable hydrophilic polyurethane polymer which may be obtained from the Organic Chemicals Division of the W. R. Grace & Company. This is a porous material and includes interconnecting pores. The insert may be held in place by an interference fit.

Figure 4:
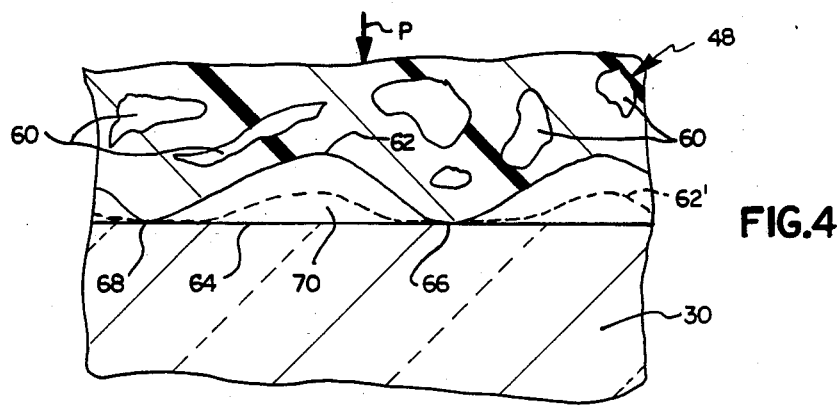
FIG. 4 is an enlarged view showing a portion of a transducer member in surface engagement with an uncladded core and used for purposes of explanation herein.

Reference is now made to FIG. 4 which is an enlarged sectional view showing a portion of the length of the uncladded optical fiber core 30 in engagement with a transducer insert 48. The transducer insert is made of a sponge-like material and has interconnecting pores 60. The interior surface 62 of the transducer insert is irregular in shape and makes intermittent surface contact with the surface 64 of the uncladded core 30, such as at locations 66 and 68 separated by an air pocket 70. The air pockets 70 are vented to the atmosphere by way of pores 60 and the annular space surrounding the cladded core within the lumen of the catheter 10 and which leads to the aperture 14 located near the proximal end of the catheter. This, then, provides the basis for a pressure differential with exterior applied pressure. As the pressure P increases, the interior surface 62 of the insert will move toward the uncladded surface 64, as indicated by the dotted lines 62', so as to increase the surface area contact with the uncladded surface 64. Likewise, as the pressure is removed, the sponge-like material, being resilient, will return to that as indicated by the solid line 62 and make less surface area contact with the uncladded surface 64. These variations in surface area contact between the transducer insert 48 and the uncladded surface of the optical fiber core with variations in pressure modulates the intensity of light traveling through the optical fiber. At this point, it is to be noted that the index of refraction n is different for the various materials employed. Thus, the index of refraction n for the fiber core 30 is on the order of 1.5 and for the surrounding air within the air pockets 60 and in the lumen, as vented to the atmosphere, is on the order of 1.0. The cladding 32 exhibits an index of refraction slightly less than that of the core 30. However, for light to be transmitted through filters 52 and be absorbed or refracted by the sponge inserts 48, the filters 52 must have an index of refraction greater than that of cladding 32 and, in turn, the inserts 48 must have an index of refraction greater than that of the filters so as to refract light that is passed by the filters.

Figure 5A:
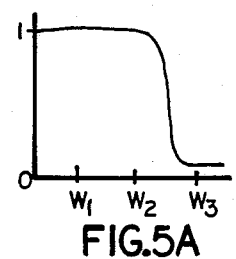
FIGS. 5A, 5B and 5C are graphical waveforms illustrating reflectivity versus wavelength useful in the description of the embodiment shown in FIGS. 2 and 3.
Figure 5B:
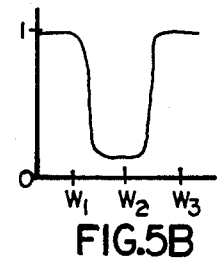
Figure 5C:
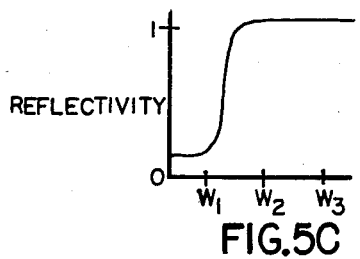
Figure 6A:
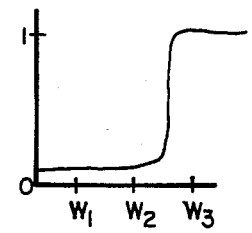
FIGS. 6A-6C are graphical waveforms illustrating light transmission as a function of wavelength and which is useful in the description of the embodiment of FIGS. 2 and 3.
Figure 6B:
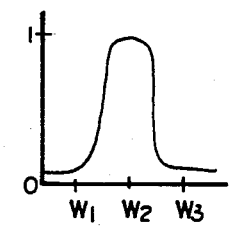
Figure 6C:
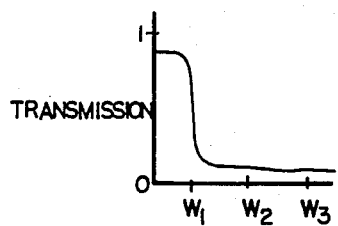

Each of the filters 52A, 52B and 52C pass light within a particular waveband and reflect the remaining light. Thus, for example, filter 52A reflects light within a waveband containing wavelengths $W_1$ and $W_2$ while passing light within a waveband containing light of wavelength $W_3$. This is illustrated in FIGS. 5A and 6A. Similarly, filter 52B passes light only within a waveband containing light in wavelength $W_2$, but reflects all remaining light, and this is illustrated in FIGS. 5B and 6B. Also, filter 52C passes light in a waveband containing wavelength $W_1$ while reflecting all remaining light, and this is illustrated in FIGS. 5C and 6C.

In this embodiment, the light source emits a broad band of light. A filament lamp or an arc lamp or other wideband light source may be employed as the light source 20. This light is passed by a beam splitter 22 and focused, as with a lens 74, into the proximal end of the optical fiber 12. The light that travels through the core 30 and which strikes the core-air interface (see FIG. 4) will be totally internally reflected. However, the light that strikes the core-sponge interface will be partially refracted and partially reflected. The amount of light that is refracted and thereby absorbed will be a function of the surface contact area. Thus, light that is traveling from the proximal end to the distal end of the catheter will pass through the transducer area and a portion of the light will be refracted in dependence upon the pressure P. The light that is internally reflected will be reflected back by the reflector 38 at the distal end of the optical fiber. This reflected back light will again be attenuated as it passes the transducer area as it travels back toward the proximal end of the catheter. The intensity of light returning at the proximal end of the catheter will vary inversely with the pressure applied to the transducers.

At transducer $T_A$, only light that has been passed by filter 52A will be refracted and, hence, attenuated by the transducer insert 48. This light will be at wavelength $W_3$ and the remaining light is reflected by the filter 52A. Consequently, it is the light which exits from the proximal end of the optical fiber 12 at wavelength $W_3$ that includes the intelligence representing the pressure applied at transducer $T_A$.

In similar fashion, it is only the light exiting from the proximal end of the optical fiber at wavelength $W_2$ that includes the intelligence relative to the pressure applied at the transducer $T_B$. Also, it is only the light exiting from the proximal end of the optical fiber at wavelength $W_1$ that includes the intelligence as to the pressure at the transducer $T_C$.

Figure 7:
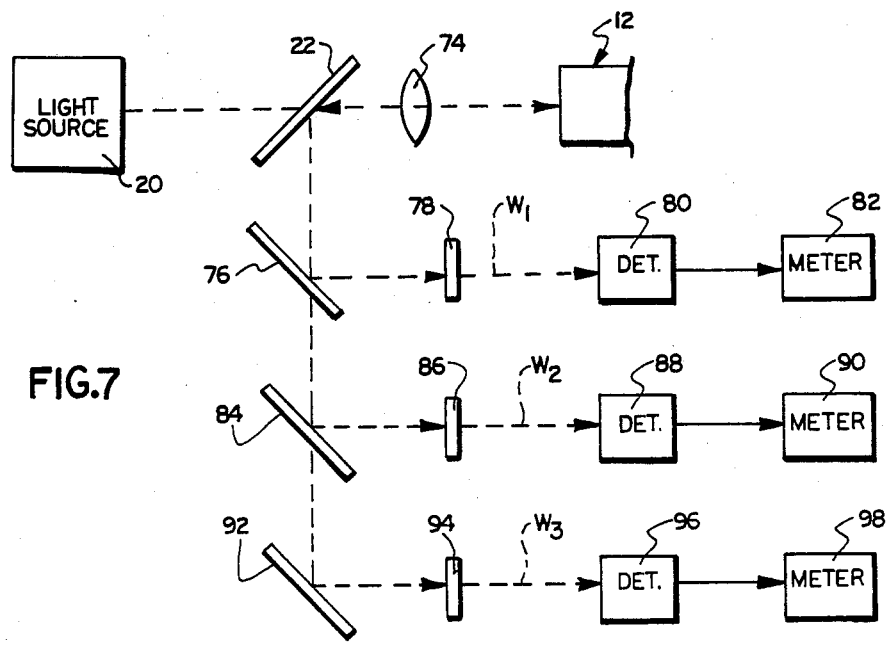
FIG. 7 is a schematic-block diagram illustration of the optical system as well as the electronic detecting circuitry employed in the embodiment of FIGS. 2 and 3.

Referring now to FIG. 7, it is seen that as the light exits from the proximal end of the optical fiber 12, it is applied by way of lens 74 to the beam splitter 22 and a portion is then directed in a downward direction. A first beam splitter 76 intercepts this light and directs a portion of it through a filter 78 that passes only light at wavelength $W_1$. This is detected by optical-electrical detector 80, which converts intelligence into an electric signal to drive a suitable meter 82 to provide an output indicative of the pressure at the transducer $T_C$. As the pressure at transducer $T_C$ increases, there will be a reduction in the amount of light returned to the proximal end at wavelength $W_1$. This is detected by detector 80 and displayed as with meter 82.

In a similar fashion, the light that is passed by the beam splitter 76 strikes a second beam splitter 84 and light reflected therefrom is passed through a filter 86 which passes light only at wavelength $W_2$. Detector 88 converts this information into an electrical signal which is supplied to a suitable meter 90. This circuitry provides an output indication representative of the pressure at transducer $T_B$. Also, light passing through the beam splitter 84 will strike a mirror 92 causing light reflected therefrom to be applied to a filter 94 which passes only light at wavelength $W_3$. This is detected by a suitable detector 96 which supplies an electrical signal to meter 98 for displaying an output signal representative of the pressure applied at transducer $T_A$.

Reference is now made to a second embodiment of the invention which is illustrated in FIGS. 8, 9, 10, 11 and 12. This embodiment is quite similar to that described thus far and, consequently, like components are identified with like character references and only the differences over the previous embodiment will be described in detail herein.

In this embodiment, no filters are employed. Instead, each of the transducer inserts 48A', 48B' and 48C' is doped with a different fluorescent dye. Each insert is covered on its exterior surface with a membrane, such as membranes 50 constructed in the same manner as that discussed herebefore with respect to membranes 50 in FIGS. 2 and 3. The fluorescent dye doped transducer inserts have been doped such that each fluoresces in a different waveband.

Figure 10A:
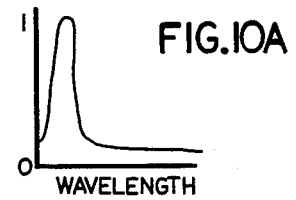
FIGS. 10A-10C are graphical waveforms illustrating excitation amplitude with respect to wavelength and is useful in describing the embodiment of FIGS. 8 and 9.
Figure 10B:
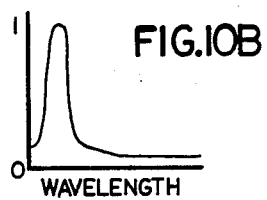
Figure 10C:
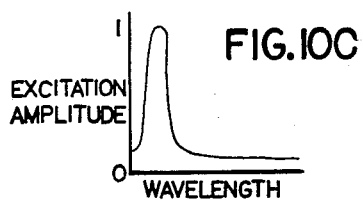
Figure 11A:
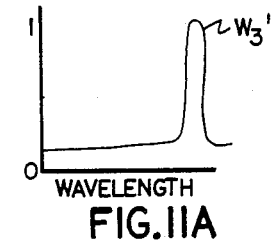
FIGS. 11A-11C are waveforms of emission amplitude versus wavelength and which is useful in describing the embodiments of FIGS. 8 and 9.
Figure 11B:
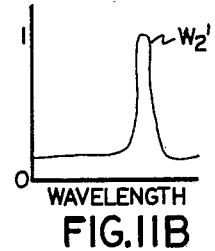
Figure 11C:
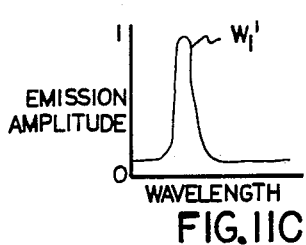
Figure 12:
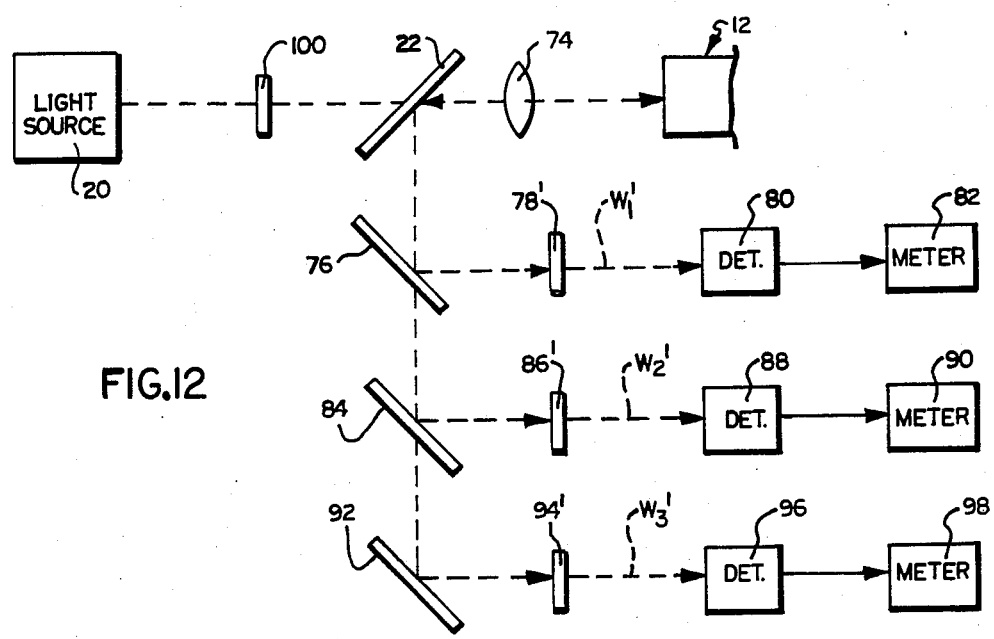
FIG. 12 is a schematic-block diagram illustration of the detector circuitry employed in conjunction with the embodiment of FIGS. 8 and 9.
Figure 13:
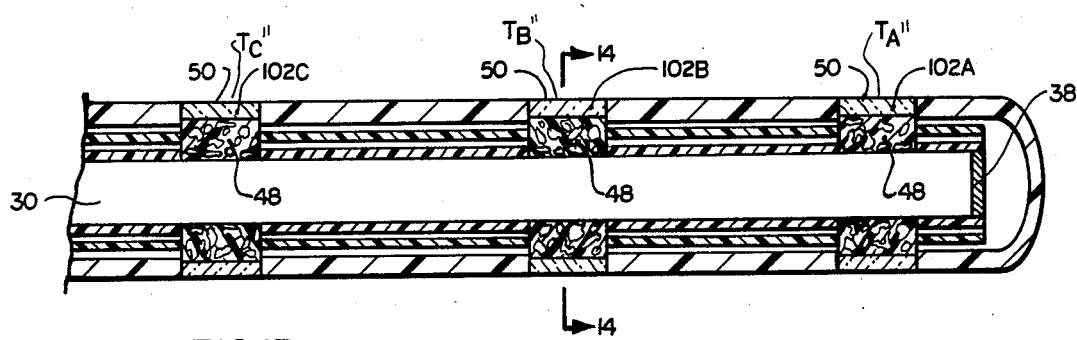
FIG. 13 is an enlarged sectional view of the distal end of the catheter showing a third embodiment of the invention.
Figure 14:
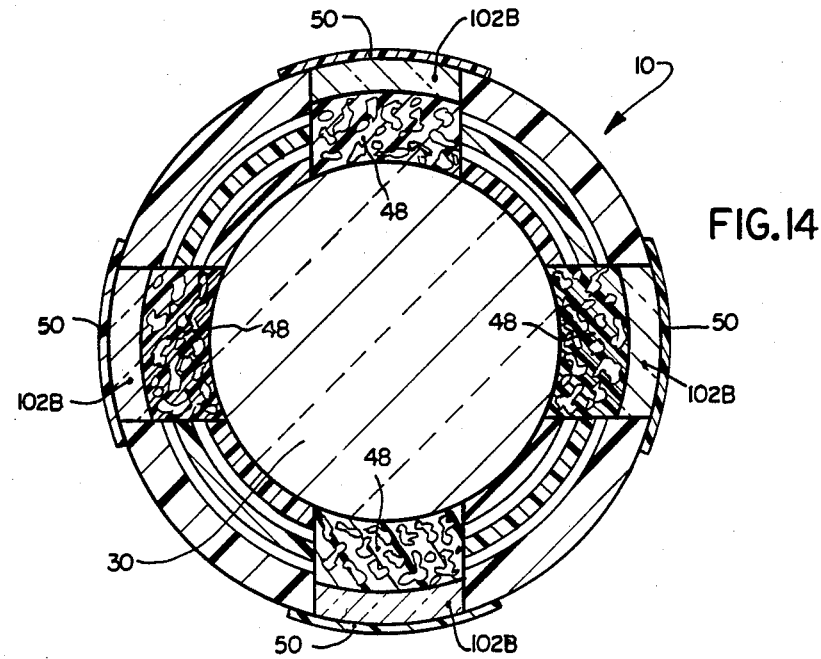
FIG. 14 is a cross sectional view taken along line 14—14 looking in the direction of the arrows in FIG. 13.

Reference is also made to FIGS. 10, 11 and 12. In this embodiment, light transmitted into the optical fiber core 30 includes light at wavelengths capable of exciting the fluorescent doped inserts 48A', 48B' and 48C', but no light is transmitted at the wavelengths at which these inserts fluoresce. For this reason, a filter 100 is employed for transmitting light only in the excitation waveband of from approximately 300–350 nanometers. This filtered light is then passed by the beam splitter 22 and focused by lens 74 into the proximal end of the optical fiber 12. Within the catheter, the excitation light will be transmitted by core 30. This excitation light is at the excitation wavelengths from 300–350 nanometers and does not include light at a wavelength corresponding to that at which the fluorescent doped transducers fluoresce. In the example given, the excitation wavelengths may be considered a waveband which includes wavelengths from 300–350 nanometers, as is illustrated in FIGS. 10A, 10B and 10C. The transducer inserts will fluoresce at higher wavelengths with that of transducer insert 48C' having an emission wavelength of $W_{1'}$ on the order of 370 nanometers. The insert 48B' will have an emission wavelength $W_{2'}$ which will be on the order of 400 nanometers, and transducer 48A' will fluoresce at a wavelength $W_{3'}$ on the order of 430 nanometers.

Thus, light passing through the optical fiber 10 within the core 30 will be refracted by the transducers 48A', 48B' and 48C' in accordance with the pressure exerted at each transducer. The greater the applied pressure, the greater will be the refraction of light. Consequently, the greater the pressure, then, the greater will be the amplitude or amount of energy emission at wavelengths $W_{1'}$, $W_{2'}$ and $W_{3'}$. Light exiting from the proximal end of the optical fiber 12 will contain light at each of these wavelengths $W_1'$, $W_2'$ and $W_3'$. This light is reflected in part by the beam splitter 22 (FIG. 12) and directed downwardly to the beam splitter 76. A portion of the light striking beam splitter 76 is reflected through a filter 78' which passes only light centered at the wavelength $W_1'$ indicative of the amount of pressure in transducer $T_C'$. This is detected by detector 80 and an electrical signal representative of the pressure level in tranducer $T_C'$ is then displayed as with meter 82. Similarly, a portion of the light passed through the beam splitter 76 to a beam splitter 84 which reflects a portion of the light to a filter 86' which passes only light centered about the wavelength $W_2'$. This is indicative of the amount of pressure at transducer $T_B'$ and this is converted into an electrical signal by detector 88 with the pressure reading then being displayed as with meter 90.

Also, a portion of the light is passed through a beam splitter 84 and is reflected by mirror 92 to a filter 94' which passes only light centered about wavelength $W_3'$. This is indicative of the amount of pressure at transducer $T_A'$ and this is converted into an electrical signal by detector 96 and the electrical output is supplied to meter 98 for providing a visual readout.

Reference is now made to FIGS. 13-16 which illustrate a third embodiment of the invention. This embodiment is similar to that described hereinbefore and like components will be identified with like character references and only the differences between this embodiment and the previously described embodiments will be described below in detail.

Figure 8:
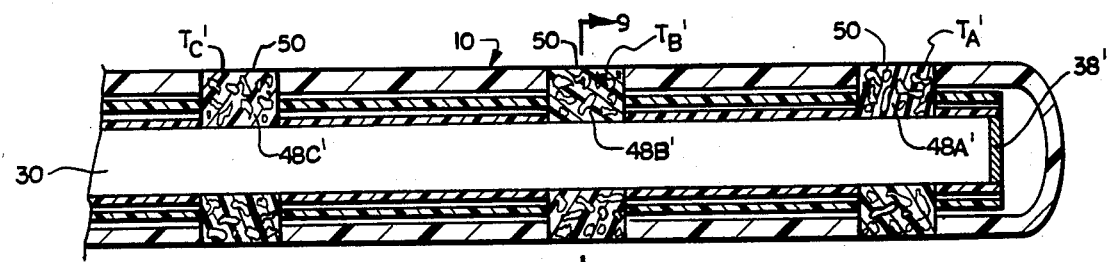
FIG. 8 is an enlarged sectional view of the distal end of the catheter showing a second embodiment of the invention.
Figure 9:
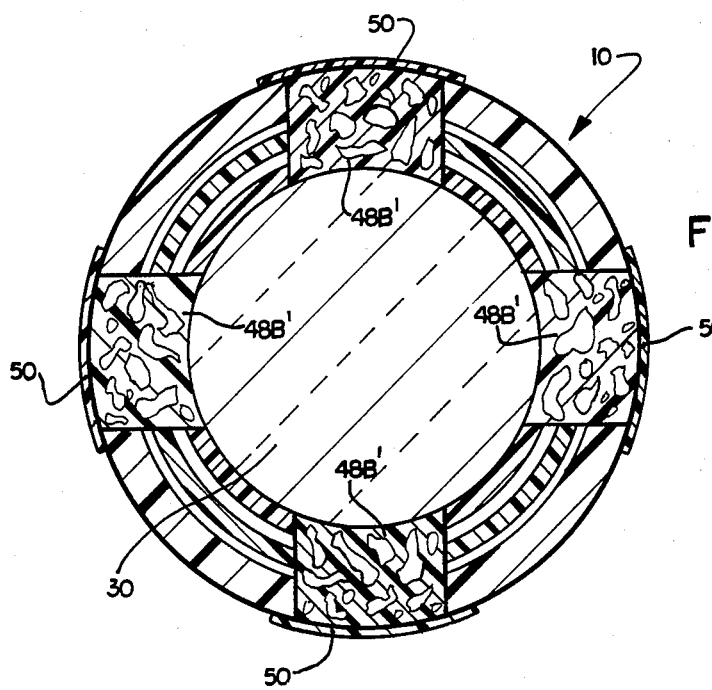
FIG. 9 is an enlarged cross sectional view taken along line 9—9 looking in the direction of the arrows in FIG. 8.

In this embodiment, as in the embodiment shown in FIGS. 8 and 9, the inserts 48 are mounted directly onto the uncladded surface areas of core 30. However, these inserts are not doped as in the case of inserts 48A', 48B' and 48C' of FIGS. 8 and 9. In this embodiment, a flexible, filter coating is applied to the exterior surface of each transducer insert. These filters are illustrated in the drawings as filters 102A, 102B and 102C applied respectively to the exterior surfaces of the transducer inserts 48. The filters, in turn, are each covered by means of a membrane 50, as in the other embodiments. The filters are sufficiently thin and flexible to transmit pressure to the inserts.

In this embodiment, the transducers are constructed from a nonabsorbent clear sponge-like material exhibiting an index of refraction greater than that of the cladding 32. Thus, the sponge-like material is transparent to light at all wavelengths. The surrounding filters, however, serve to pass light of a particular wavelength and reflect all other wavelengths. For example, light passing through insert 48 at wavelength $W_1''$ will be refracted by filter 102c and absorbed. Light outside of this waveband will be reflected by the filter and/or by the surrounding cladding 50 and passed back through the insert into core 30. Similarly, at transducer $T_B''$, light which has been passed by the clear transducer insert 48 will be passed to the filter 102B which will, in turn, pass or absorb only light at wavelength $W_2''$, with the remaining light being reflected back into the core. Also, at transducer $T_A''$, light passing through the transducer insert 48 at wavelength $W_3''$ will be, in turn, passed by the filter 102a with the remaining light being reflected back into the core 30. This is indicated by the waveforms of FIGS. 15A-15C.

White light supplied by source 20 (FIG. 16) is passed by a beam splitter 22 and focused by a lens 74 into the proximal end of the optical fiber 12. The returning light includes information respecting the pressures at the three transducers in the sense of changes in the amount of light received at wavelengths $W_1''$, $W_2''$ and $W_3''$ from that which was originally introduced at those wavelengths into the optical fiber. For example, the returning light includes light at wavelength $W_1''$. Consequently, the returning light is reflected by beam splitters 22 and 76 and applied to a filter 78'' which passes only light at wavelength $W_1''$. This is detected by detector 80 and converted into an electrical signal which is supplied as one input into a ratio circuit 120.

Light which is reflected from the splitter 22 in an upward direction is supplied to a second beam splitter 122 which reflects a portion of that light through a filter 124. This filter serves to pass light only at wavelength $W_1''$ to a detector 126 which provides an electrical signal to a second input of the ratio circuit 120. The ratio circuit, then, compares the amplitude of light at wavelength $W_1''$ as it enters the optical fiber 12 with that which returns from the optical fiber to obtain a normalized signal. This signal, identified as $V_1$, is then supplied to a suitable meter, such as meter 82, calibrated to provide an output pressure indication at transducer $T_C''$ as a function of the signal $V_1$. It is to be understood that FIG. 7 could be depicted similarly to improve the signal.

In a similar manner, the light returning from the optical fiber at wavelength $W_2''$ is detected and supplied to a second ratio circuit 130. In this case, the light which passes through splitter 122 is reflected from another splitter 132 and is supplied to a filter 134 which passes light only at wavelength $W_2''$, and this is detected by a detector 136. Detector 136 operates to provide an electrical signal to the second input of the ratio circuit 130 representative of the intensity of light at wavelength $W_2''$ as it originally entered the optical fiber 12. The ratio is determined by the ratio circuit 130 as output signal $V_2$ and this is supplied to meter 90 which is calibrated to provide an output indicative of the pressure at transducer $T_B''$ as a function of signal $V_2$ Also, light returning from the optical fiber 12 at wavelength $W_3''$ is passed by the filter 94'' and detected by detector 96 and the electrical output signal therefrom is supplied to another ratio circuit 140. Light passing through the beam splitter 132 is reflected from a mirror 142 and passed to a filter 144 which passes only light at wavelength $W_3''$. This is detected by detector 146 which supplies an electrical output signal to a second input of the ratio circuit 140. The circuit 140, in turn, provides an output signal $V_3$ which is supplied to a meter 98 calibrated to provide a pressure reading as a function of signal $V_3$.

Although the invention has been described in conjunction with preferred embodiments, it is to be appreciated that various modifications may be made without departing from the spirit and scope of the invention as defined by the appended claims.

Having described specific preferred embodiments of the invention, the following is claimed:

1. Apparatus for use in simultaneously measuring fluid pressure at multiple sites at remote locations within a body cavity, comprising:
   a single elongated optical fiber member having a light transmitting core coaxially surrounded by cladding means essentially throughout its length, said core being uncladded for a plurality of portions of its length proximate to the distal end thereof;
   a pressure transducer means located adjacent each said uncladded portion, each pressure transducer means including a flexible transducer member having an irregular surface facing a said uncladded core portion for making surface area contact therewith such that the contacting surface area varies with pressure forces applied to said transducer member acting transversely of said uncladded core portion, said transducer member being constructed of material exhibiting a greater index of refraction than said cladding means so that the intensity of light passing through said core proximate to said transducer means is modulated in its intensity as a function of said pressure forces; and
   each said transducer means including light wavelength dependent means for modulating light at a particular wavelength different from that of said other transducer means.

2. Apparatus as set forth in claim 1 wherein each said transducer means includes a filter means for passing light within one wavelength range while reflecting light of other wavelengths.

3. Apparatus as set forth in claim 2 wherein said filter means is interposed between a said uncladded core portion and a said transducer member so that only light passed by said filter means is modulated by said transducer member as a function of said pressure forces.

4. Apparatus as set forth in claim 3 wherein each said filter means exhibits a different index of refraction and each being greater than that of the index of refraction of said cladding means.

5. Apparatus as set forth in claim 4 wherein each said transducer member exhibits an index of refraction greater than that of the associated said filter means.

6. Apparatus as set forth in claim 3 including reflecting means located at the distal end of said optical fiber member for reflecting light back through said core to the proximal end of said optical fiber member so that light passing through said optical fiber member is modulated twice by each of said transducer members.

7. Apparatus as set forth in claim 6 including means for supplying light into the proximal end of said optical fiber member and detector means for receiving light exiting from said proximal end, said detector means including means for detecting the amount of light in each of said wavelengths for simultaneously providing a corresponding plurality of output indications representing the pressure forces acting on each of said transducer members.

8. Apparatus as set forth in claim 2 wherein each said transducer member has an outer surface and each said filter means is located adjacent the outer surface of a said transducer member each said transducer member is constructed of optically transparent material so that light passed from said uncladded core portion into said transducer member is modulated thereby and only light within a given wavelength range is absorbed by said filter means.

9. Apparatus as set forth in claim 8 including reflecting means located proximate to the distal end of said optical fiber member for reflecting light back through said core to the proximal end of said optical fiber member so that light passing through said core is modulated twice by each of said transducer members.

10. Apparatus as set forth in claim 9 including means for supplying light into the proximal end of said optical fiber member and detector means for receiving light exiting from said proximal end, said detector means including means for detecting the difference in the intensity of light transmitted into and received from said proximal end at each of said wavelengths and simultaneously providing output indications of the pressure forces acting on each of said transducer members as a function of said detected differences.

11. Apparatus as set forth in claim 1 wherein said light wavelength dependent means includes means doping each said transducer member with fluorescent dye, said transducer members at the different transducer means being doped with different fluorescent dyes so that when excited by light each will fluoresce and emit light at a different wavelength such that the emission level at a given wavelength associated with a specific transducer means varies in dependence upon pressure applied to that transducer means.

12. Apparatus as set forth in claim 11 including reflecting means proximate to the distal end of said optical fiber member for reflecting light back through said core to the proximal end thereof so that light passing through said optical fiber member is modulated twice by each said transducer means.

13. Apparatus as set forth in claim 12 including means for supplying light into the proximal end of said optical fiber member wherein the supplied light is within a waveband including wavelengths different than that of the emission wavelengths of each of said transducer means.

14. Apparatus as set forth in claim 13 including detector means located proximate to the proximal end of the said optical fiber member for receiving light exiting therefrom, said detector means including means for detecting the amount of light at each of said emission wavelengths for simultaneously providing output indications of the pressure forces acting on each of said transducer means.

* * * * *